United States Patent [19]

Baldwyn

[11] Patent Number: 4,836,038
[45] Date of Patent: Jun. 6, 1989

[54] AUTOMATED SAMPLER-INJECTOR APPARATUS AND METHOD FOR SAMPLING A QUANTITY OF SAMPLE AND TESTING PORTIONS OF SAID QUANTITY

[75] Inventor: Einar D. N. Baldwyn, Calgary, Canada

[73] Assignee: Aim Instruments Ltd., Calgary, Canada

[21] Appl. No.: 169,876

[22] Filed: Mar. 18, 1988

[51] Int. Cl.⁴ .............................................. B01L 3/02
[52] U.S. Cl. .............................. 73/864.21; 73/864.25; 422/64
[58] Field of Search ........... 73/863.01, 863.72, 863.73, 73/864.21, 864.22, 864.23, 864.24, 864.25, 864.81, 864.83, 864.84, 864.85; 422/64, 67, 70

[56] References Cited

U.S. PATENT DOCUMENTS

| | | | |
|---|---|---|---|
| 3,530,721 | 9/1970 | Hrdina | 73/863.72 |
| 4,068,529 | 1/1978 | Konig | 73/864.24 |
| 4,311,667 | 1/1982 | Gocho | 73/864.24 |
| 4,478,095 | 10/1984 | Bradley et al. | 73/864.21 |
| 4,577,515 | 3/1986 | Someya et al. | 73/864.83 |
| 4,756,201 | 7/1988 | Uffenheimer | 73/864.83 |

Primary Examiner—Michael J. Tokar
Assistant Examiner—Robert R. Raevis
Attorney, Agent, or Firm—Gowling & Henderson

[57] ABSTRACT

An automated sampler-injector apparatus and method of sampling, for taking samples from multiple sources and repetitively injecting small portions of a quantity sampled from a single source into a liquid chromatograph column for analysis. The apparatus comprises a syringe and injector tube forming a syringe loop for drawing a quantity of sample from a sample container. A carousel for positioning a selected sample container beneath the syringe loop is provided, and an injector valve having a sample loop therein is further provided for receiving portions of a quantity of sample from the syringe loop and retaining such portion in the sample loop and further transferring the portion of sample from the sample loop into a liquid chromatograph for analysis. The method comprises a procedure for utilizing the apparatus so as to repetitively inject portions of the sampled quantity into the valve, switching the valve from a load position to an inject position to inject the portion of sample into the liquid chromatograph, and repeating the process until the quantity of sample contained in the syringe loop is exhausted.

10 Claims, 5 Drawing Sheets

4,836,038

AUTOMATED SAMPLER-INJECTOR APPARATUS AND METHOD FOR SAMPLING A QUANTITY OF SAMPLE AND TESTING PORTIONS OF SAID QUANTITY

INTRODUCTION

The present invention relates to improvements in automated sampling apparatus and methods for taking a quantity of sample from multiple sources for testing in analytical instruments. More particularly the present invention relates to an automated sampling apparatus and method of sampling for repetitive injection of portions of a sampled quantity into a liquid chromatograph device for analysis.

BACKGROUND OF THE INVENTION

Numerous known patented devices exist in the art of automated sampling of multiple sources for analysis in liquid chromatograph devices.

In early liquid sampling devices, typified in U.S. Pat. No. 4,478,095 to Bradley, et al, and containing samples were disposed around the periphery of a rotatable turntable or carousel.

These devices used a positive displacement system for drawing up a quantity of sample from the vials, wherein a co-axial needle was used to pierce a septum covering the vials, and air or an inert gas injected through an outer annulus within the co-axial needle to force a quantity of sample up through the inner annulus of the needle into a conduit means.

The quantity of sample was then conveyed by the conduit means to an injector valve, and into a sample loop affixed at both its inlet end, and outlet end, to such injector valve. The rotary component of the valve was then rotated to connect one end of the sample loop with a supply of pressurized solvent, and the other end of the sample loop was placed in communication with a conduit leading to a liquid chromatograph column. The quantity of sample was thereby flushed from the sample loop by the pressurized solvent, and thusly flowed into the chromatograph column together with the solvent for analysis.

FIG. 1 of U.S. Pat. No. 4,478,095 to Bradley et al clearly shows such a device, having a conduit 49 leading from the vials to an injector valve 51, and also a syringe means 139 for aiding the withdrawal of the quantity of sample from the vials 27. The quantity of sample is drawn into the sample loop 143 connected to the injector valve 51, and the valve is then switched to connect a pressurized flow of solvent in conduit line 153, which then flushes the quantity of sample into conduit line 155 for transfer to a liquid chromatograph column.

FIGS. 4 and 5 of U.S. Pat. No. 3,918,913 disclose a similar device for withdrawing a quantity of sample from a vial 11, and injecting such quantity into a liquid chromatograph column 6, operating on the identical principal.

The problem with such prior art devices was that a portion of the sampled quantity always lay in the conduit line leading from the sample container to the injection valve, and was never able to be injected into the column for analysis.

Accordingly, only sample volume which lay in the sample loop (line 5 in FIGS. 4 and 5 of Stevenson et al, and line 143 in FIG. 1 of Bradley et al) was able to be injected into the liquid chromatograph column for analysis, and the portion of the sampled volume lying in the conduit line leading to the valve (conduit line 21 in FIGS. 4 and 5 of Stevenson et al, and conduit line 49 of FIG. 1 of Bradley et al) was unusable, and had to be purged from the system by means of flushing solvent, as disclosed in U.S. Pat. No. 4,478,095 to Bradley et al, to avoid contamination with a subsequently drawn quantity of sample from another sample container.

In some applications for sampling devices, it is extremely critical to avoid any loss of the sampled quantity, since as much as possible of the sampled quantity is desired to be injected into the liquid chromatograph for analysis. For example, in hospital and medical use, the quantity of sample contained in vials where the sample is a blood, tissue, or bone marrow specimen obtained from a child, or a small localized area of infection in an individual, may indeed be a very small quantity, often much less than 20–100 microliters.

Accordingly, as much as the sample must be injected as possible into the liquid chromatograph column to obtain as accurate an analysis as possible of the components within the sampled quantity.

In order to overcome the problem of sample loss, it is known in the prior art to incorporate the sampling conduit line as part of the sample loop, whereby all of the sampled quantity can then be injected through the injector valve into the liquid chromatograph column.

U.S. Pat. No. 4,242,909 to Gundelfinger, assigned to Rheodyne Incorporated, discloses such a device. Accordingly, in FIGS. 7 and 8 thereof, an injector valve 156 in a load position allows the valve ports on the injector valve to connect a syringe means 19 with an overfill loop 18 whose loop end 22 is inserted into a sample container 12 to allow the syringe means 19 to withdraw a sample therefrom. The injector valve 156 when switched to an inject position, operatively disconnects the overfill loop 18 with the syringe means 19 and connects one end thereof 44 to a pressurized flow of solvent, and the other end (i.e. the loop end 22) is allowed to be inserted into a loop end coupling 152 in injector valve 154, which is in fluid communication with the liquid chromatograph column 14.

While the Gundelfinger configuration completely overcomes the problem of sample loss, since all of the sampled quantity drawn into the overfill loop 18 is injected into the injector valve 154 and into the liquid chromatograph column 14, and further that by placing the loop end 22 directly into the injector valve 154, certain other advantages discussed below are realized, a definite and important drawback of the Gundelfinger configuration lies in the fact that all of the quantity drawn into the overfill loop 18 must be injected at one time into the injector valve 154 and chromatograph column. Accordingly, because the overfill loop 18 comprises part of the flow line between the high pressure pump 32 and liquid chromatograph column, no capability exists for repetitively injecting aliquot portions of the sampled quantity from the overfill loop 18 to the chromatograph column. This is important, since duplicate or triplicate results from chromatograph testing cannot be obtained, which greatly lessens confidence in the single result thereby obtained.

The Gundelfinger type configuration accordingly presents serious disadvantages then in pharmaceutical or immunilogical testing applications, since frequently the testing regimen specified in laboratory procedures requires repetitive liquid chromatograph testing on the same sampled quantity. Accordingly, for the Gundelfinger configuration to accomplish this result, only a portion of the sample contained within the sample container can be withdrawn at one time for analysis. This requires much greater complexity in the apparatus to accomplish this result, and the applicant herein presently knows of no device using such configuration that has been able to accomplish this result.

Accordingly, a real need exists in the art for a sampling device that is able to utilize all of the sampled quantity for subsequent injection into a liquid chromatograph column without sample loss, and further be able to repetitively inject equal portions of the same sampled quantity into a liquid chromatograph column to thereby improve the reliability in the results obtained from such liquid chromatograph testing.

As mentioned above, the placement of a loop end, or injector tube, directly into an injector valve, wherein the loop end within the valve is then allowed to be in direct fluid communication with the sample loop, avoids the problem that of the earlier valve designs had in that some of the sample would remain in the flow passage of the injector valve between the injector tube and the sample loop, and thus not be injected. This advantage is known in the art, and is clearly disclosed in U.S. Pat. No. 4,182,184 to Bakalyar, also assigned to Rheodyne, which relates to an injector valve specifically incorporating such feature.

Such patent discloses a manual method, however, for use of such injector valve wherein a micro-syringe 52, as shown in FIG. 6 thereof, is inserted into the injector valve 50 to inject an entire previously sampled quantity into a sample loop 72, and the rotor 58 of the injector valve 50 is rotated, as shown in FIG. 8 thereof, to connect the sample loop 72 at one end with a pressurized source of solvent, and at the other end with a liquid chromatograph column, to flush the sample into the liquid chromatograph column.

The Bakalyar patent does not, however, teach or disclose the method of injecting aliquot portions down to 1-10 microliters in volume from a single sampled quantity of sample previously drawn into the micro syringe, and then switching the injector valve 50 from a load position to an inject position and back to a load position, to repetitively inject portions of such sampled quantity into the liquid chromatograph column. In fact, such patent clearly discloses at page 3, lines 65-68 thereof that the sample loop is always made long enough to contain a volume of liquid greater than the largest volume to be introduced by the micro syringe 52.

To achieve the ability to repetitively inject microliter portions of a sampled quantity into the injection valve from a syringe means, automation of the injection valve and syringe means are required, since manual sensitivity is not adequate to dispense such small volumes from the micro syringe into the injection valve.

It was not immediately apparent then from the prior art how the Bakalyar injection valve with its above advantages may be automated. This was due to the fact that in most applications the syringe needle passageway 104 was contemplated as being located in the rotor, offset from the axis of rotation thereof, and accordingly rotation of the rotor moved the syringe needle passageway making it difficult for automatic means to align the syringe needle with the syringe passageway in the valve.

U.S. Pat. No. 4,242,909 to Gundelfinger, a later patent also assigned to Rheodyne Incorporated does disclose in FIGS. 7 and 8 thereof an automated sampler-injector design utilizing the Bakalyar valve. However, as discussed earlier, such configuration only allowed the entire contents of the overfill loop 18 to be injected into the injector valve 156, and accordingly aliquot portions of the sampled quantity were unable to be dispensed into the valve. Moreover, such patent clearly disclosed on page 6, lines 61-68 and page 7, lines 1-13 that the tube receiving passage 152 located in the rotor was to be rotated. Accordingly, since the loop end 22 can only be inserted into the loop end receiving passage 152 when such passage is aligned with the liquid chromatograph column 14, should the column be under pressure, it is possible leakage of the solvent from the column 14 could occur from the loop-end receiving passage 152, and also leakage of the sample contained in the overfill loop 22 from the loop end 22, up to the point in time the loop end 22 is lowered into the loop-end passage 152 for injection of the sample into the valve 156. Accordingly, it is unclear from Gundelfinger precisely how the Bakalyar valve is to function effectively within the parameters of the design disclosed in Gundelfinger.

SUMMARY OF THE INVENTION

In order to overcome the disadvantages inherent in the prior art configurations for automatically sampling and analyzing samples drawn from sample containers, such as the problem of sample loss, and further to be able to accurately and automatically dispense multiple aliquots ranging in volume to as low as one microliter from a single sampled quantity into an injector valve for subsequent injection into a liquid chromatograph column, the present invention discloses both an automated sampler-injector apparatus, as well as a method of sampling and analyzing, which both achieve the above objects.

Accordingly, in one of its broad aspects, the sampler-injector apparatus of the present invention comprises a syringe means connected by tubing means to an injector tube to form a syringe-loop, a carousel means which holds and retains therein a plurality of sample containers, means for positioning a selected one of the sample containers immediately beneath the injector tube, means for lowering the injector tube into the selected sample container to withdraw a quantity of sample therefrom, means for raising the injector tube, means for positioning the carousel means to allow the injector tube access to an injector valve having a tube-receiving passage thereon, means for positioning the injector tube in the tube-receiving passage and operating the syringe to inject a portion of the sampled quantity from the syringe-loop into the injector valve and further into a sample loop connected to the injector valve, means for switching the valve by rotating one portion of the valve and keeping the other portion of the valve containing the tube-receiving passage stationary, to switch the sample loop from being in fluid communication with the tube-receiving passage to being connected at one end thereof to a supply of pressurized solvent, and at the other end thereof to a liquid chromatograph column, to thereby allow the portion of the sample contained in the sample loop to be flushed from the loop and injected into the liquid chromatograph column by the pressurized solvent for analysis.

Accordingly, by providing a sampler-injector apparatus of the above configuration, wherein the syringe-loop may inject the portion of aliquot of the sampled quantity directly into a sample loop for subsequent transfer and injection at high pressure by the injection valve into the liquid chromatograph column, all "dead volume" within the tubing lines is eliminated, since the syringe-loop by repetitively injecting into the sample loop is able to transfer essentially all of the sampled quantity and thus no quantity of sample is unutilized.

Further, although injection valves of the type contemplated for use in the present invention, (i.e. having a tube-receiving passage) are known for manual uses, wherein the tube-receiving passage is mounted on the rotor and extends parallel to but offset from the axis of the rotor, and moves about such axis when the rotor is rotated, (i.e. the valve is switched) while the stator to which the supply of pressurized solvent and the liquid chromatograph column are connected remains stationary, by adapting such valve to keep the portion of the valve containing the tube-receiving passage stationary, and forcing the portion of the valve to which the source of pressurized solvent, and the liquid chromatograph column are coupled to rotate, such valve is thus able to be utilized in an automated sampler-injector. Accordingly, the injector tube may now be placed within the tube-receiving passage without fear that the injector tube will be bent or broken-off when the valve is switched, since the tube-receiving passage is now held stationary, and the other portion of the valve is rotated relative thereto, rather than the reverse, as was taught in the prior art (ref. U.S. Pat. No. 4,242,909 to Gundelfinger). Thus, all of the advantages of such valve, such as those described in U.S. Pat. No. 4,182,184 to Bakalyar, are now able to be realized. More particularly, by utilizing a syringe loop and being able to inject the portion of the sample into the stationary tube-receiving passage of the valve at atmospheric pressure, and subsequently switching the valve to transfer the sample from the sample at high pressure (up to 10,000 psi), a high pressure seal at the injector tube—tube-receiving passage interface is not now required. This differs from the Gundelfinger configuration, which utilized an injector valve with a tube-receiving passage, but which required a high pressure seal at such location, because the overfill loop was actually part of the sample loop, and was accordingly subject to the pressurized solvent used for flushing the sample into the liquid chromatograph.

In another of its broad aspects, the present invention comprises a method for automatically sampling a quantity of sample and injecting in consecutive sequence portions of said quantity into a liquid chromatograph column for analysis, from each of a plurality of sample containers, comprising the steps of: (a) positioning a carousel member containing a plurality of sample containers so that a selected one of the sample containers is disposed vertically beneath an injector tube connected by tubing means to a syringe means; (b) lowering said injector tube from an original position into the selected sample container, and operating said syringe means to draw up a quantity of said sample through said injector tube into said tubing means; (c) raising said injector tube to its original position, and removing the selected sample container from beneath said injector tube so as to expose a multi-port injector valve vertically beneath said injector tube; (d) switching said multi-port injector valve so that one end of a sample loop, connected to a first port on a second element of said valve, is aligned and in communication with a tube-receiving passage located in a first element of said valve; (e) lowering said injector tube into said tube-receiving passage; (f) operating the syringe means to force a portion of the quantity of sample contained in said tubing means through said injector tube and into said sample loop, said sample loop connected at its said other end to a second port on said second element of said valve; (g) rotating said second element of said injector valve relative to said first element so that a means for flushing said portion of sample from the sample loop, connected to a third port on said valve, is in fluid communication with one of said ends of said sample loop, and a liquid chromatograph column connected to a fourth port on said second element in fluid communication with said other of said ends of said sample loop, thereby flushing the sample from the sample loop and into said chromatograph column; (h) repeating the steps (d), (f) and (g) at least once; (i) raising said injector tube to said original position; and (j) positioning said carousel member so that a further selected one of the sample containers is disposed vertically beneath said injector tube.

BRIEF DESCRIPTION OF THE DRAWINGS

Further objects and advantages will appear from the following detailed description of the invention, taken together with the accompanying drawings in which.

DETAILED DESCRIPTION OF THE INVENTION

Figure 1:
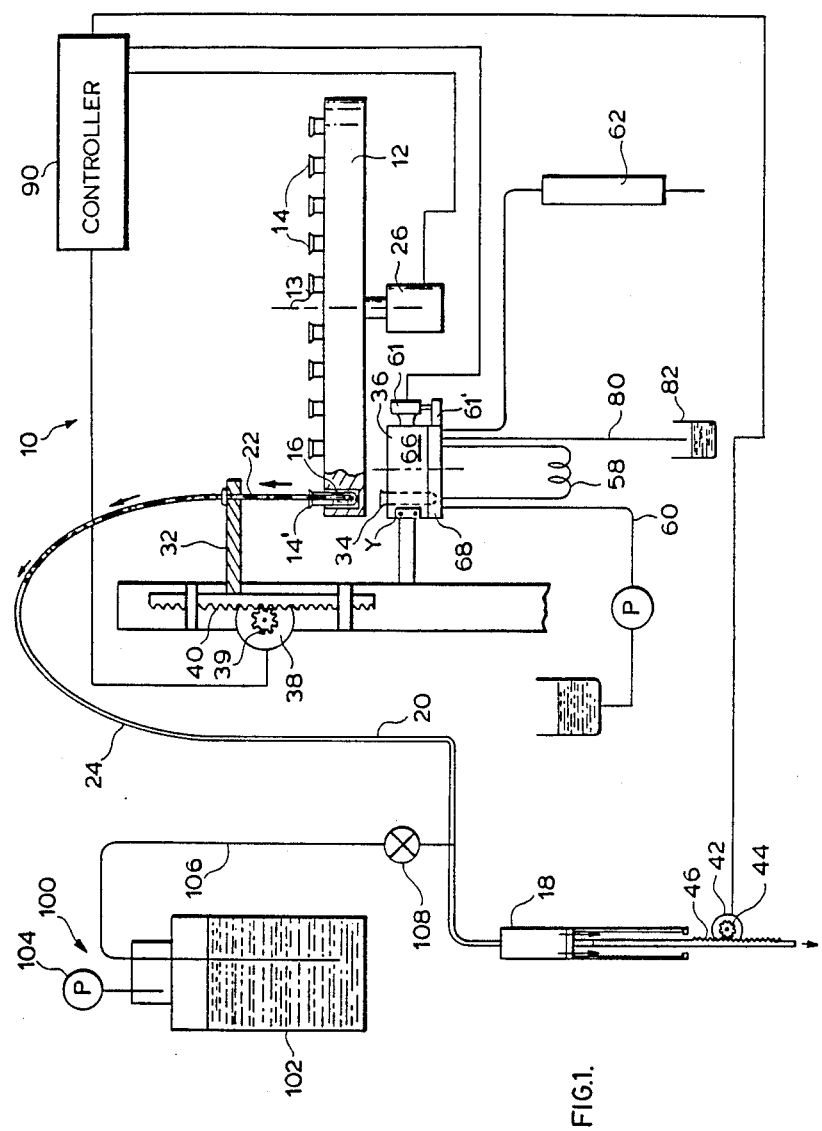
FIG. 1 is a schematic view of a preferred embodiment of the automated sampler-injector apparatus of the present invention, showing the apparatus in the sample position.
Figure 2:
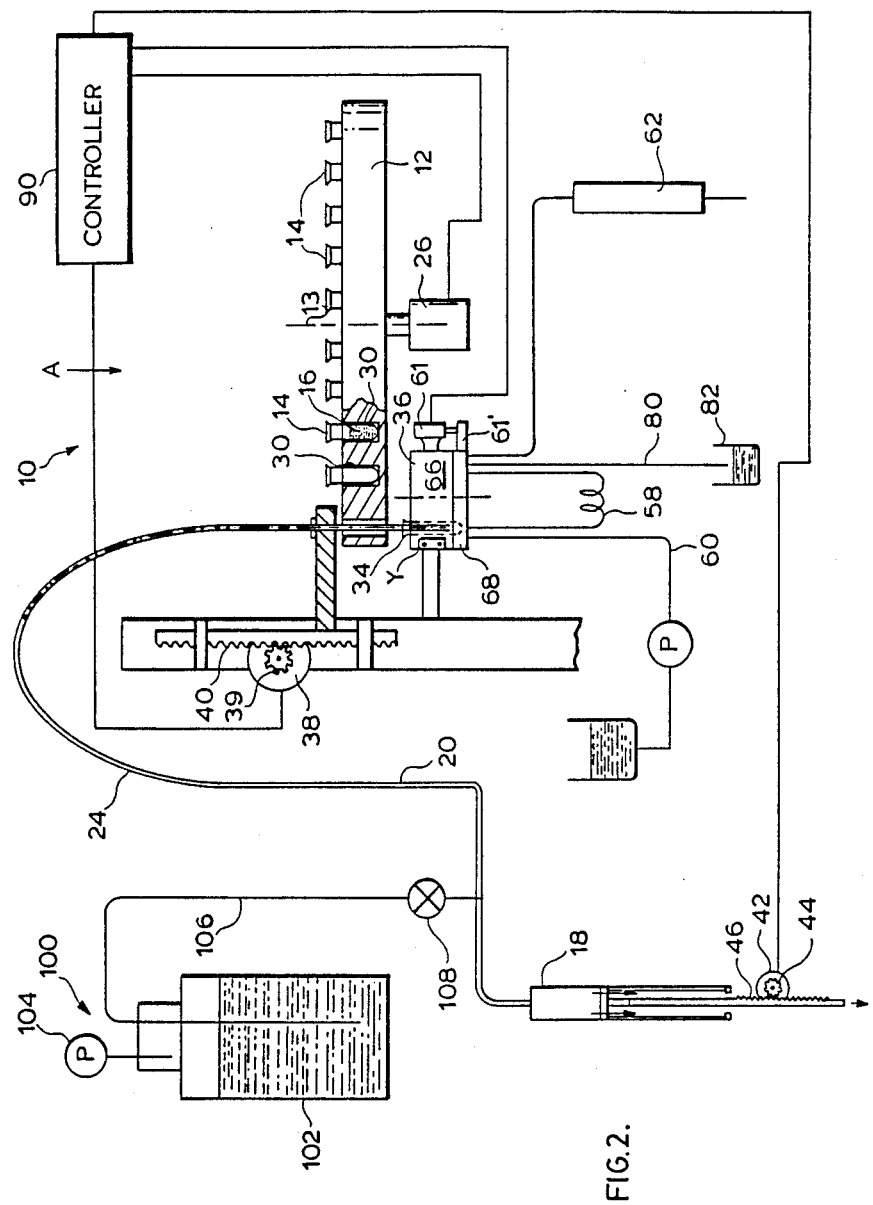
FIG. 2 is a schematic view of a preferred embodiment of the automated sampler-injector apparatus of the present invention, showing the apparatus in the load-inject position.

FIGS. 1 and 2 show an automated sampler-injector 10 of the present invention, having a carousel means 12 for holding and retaining therein a plurality of sample containers 14, each containing sample 16. Syringe means 18 is provided, connected to tubing means 20 which is in turn connected to an injector tube 22 to form a syringe-loop 24.

Means are further provided for positioning a selected one of the sample containers 14 immediately beneath the injector tube 22 to allow the injector tube 22 to be lowered into the sample container 14. In the preferred embodiment the carousel means 12 is a circular disc, and accordingly the means for positioning the sample container is a motor means 26 capable of rotating the carousel means 12 so as to position a desired sample container 14 beneath the injector tube.

Figure 3:
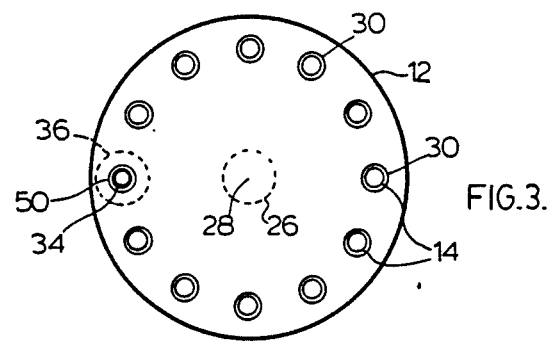
FIG. 3 is a view on arrow A of FIG. 2, showing the rotatable carousel means of the preferred embodiment of the present invention.

In the preferred embodiment, the circular disc comprising the carousel means 12 has an axis of rotation 13 perpendicular to the plane of the disc and passing through its center 28, and further a plurality of orifices 30 are provided on such carousel means 12. Such orifices 30 are aligned parallel to axis 13 and located along a common radii R about the periphery of the disc, as shown in FIG. 3.

Figure 6:
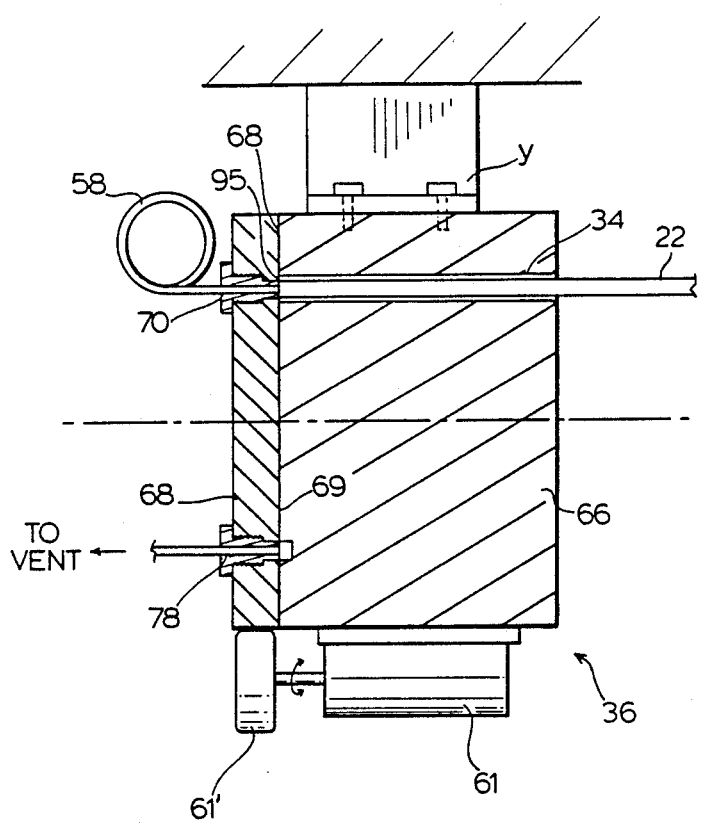
FIG. 6 is a cross-sectional view taken along plane X—X of FIG. 4.

Raising and lowering means 32 are provided to allow the injector tube 22 to be moved from an original position (not shown) to a first position inside the selected sample container 14 (see FIG. 1) and to a second position inside a tube-receiving passage 34 located within a multi-port injector valve means 36 (see FIGS. 2 and 6). The raising and lowering means 32 in the preferred embodiment consists of an electric motor 38 having a rotatable toothed pinion gear 39 driving a toothed rack 40, but other means may be used to cause raising and lowering of the injector tube 22.

Means for operating the syringe means 18 to allow withdrawal of a quantity of sample 16 from the sample containers 14 into the syringe-loop 24 may similarly comprise an electric motor 42 having a rotatable toothed pinion gear 44 driving a toothed rack 46 to which the syringe means 18 is affixed, but other means may likewise be used to operate the syringe means 18.

Means for positioning the carousel means 12 to allow the injector tube 22 access to the tube-receiving passage 34 on the injector valve 36 are also employed. In the preferred embodiment, wherein the carousel means 12 is a circular disc, such means for positioning entails utilizing the circular disc motor means 26 to rotate an aperture 50 located in the periphery of the disc and which passes in a straight line through the thickness of the disc. Once the aperture 50 is aligned immediately vertically below the injector tube 22, the injector tube may be lowered and inserted through the aperture 50, and into the tube-receiving passage 34 on the injector valve 36. Other means for allowing the injector tube access to the injector valve 36 may be used, such as mechanical means to either move the carousel means 12 away from the injector tube 22 once a sample has been drawn up, or means to move the injector tube 22 away from the carousel 12 so as to allow the injector tube 22 free access to the injector valve 36.

Means are further required to cause switching of the injector valve 36 from a first load position (FIG. 4), in which the tube-receiving passage 34 is in fluid communication with one end of a sample loop 58 to a second inject position (see FIG. 5), in which one end of the sample loop 58 is connected through the injector valve 36 to a high pressure solvent line 60 and the other end thereof is connected through the injector valve 36 to a liquid chromatograph column 62.

Accordingly, FIGS. 1, 2, 4, 5 an 6 each show a valve switching means 61,61' for carrying out the valve switching. This switching means 61,61' may be any number of mechanical or servo-mechanical means to operate the valve 36 to cause switching of the valve.

In the preferred embodiment, the valve 36 which is contemplated as being used is comprised of a first element or portion 66, which contains the tube-receiving passage 34 which extends therethrough along a straight line to a face 67 thereof. Such first element 66 is held stationary at location Y as shown in FIGS. 1 and 2. A second element or portion 68 is adapted to be rotated by said valve switching means 61,61' relative to the first element 66, and has a face 69 axially adjacent to and in bearing contact with the face 67 on the first element 66. The second element 68 possesses a first and second valve port 70 and 72 respectively, to which the sample loop 58 is connected. The second element 68 also possesses a third port 74 for connection to a high pressure supply line 60 containing solvent, and a fourth port 76 for connection to a liquid chromatograph column 62.

A fifth port 78, which is used as a vent port for discharging any unwanted contents of the sample loop 58 during the load cycle, such as for example displacing solvent remaining in such sample loop 58 from a recent cleaning cycle, is connected to a discharge tube 80 which drains into a waste receptacle 82.

In operation, the sampling, loading, and injecting steps using the automated sampler-injector device 10 of the present invention are conducted as follows:

Firstly, the carousel member 12 containing the plurality of sample containers 14 is positioned so that a selected one of the sample containers 14' is disposed vertically beneath an injector tube 22 connected by tubing means 20 to a syringe means 18, to form a syringe-loop 24, as shown in FIG. 1. Next, the injector tube 22 at the end of the syringe-loop 24 is lowered from an original position into the sample container 14', and the motor 42 which operates the syringe means 18 is activated to cause the syringe loop 24 to draw up from the sample container 14' a quantity of sample 16 through the injector tube 22. The injector tube 22 is then raised to its original position, and the selected sample container is either moved from its position beneath the injector tube 22, or means are used to move the injector tube 22, so that it has access to a multi-port injector valve 36.

Figure 4:
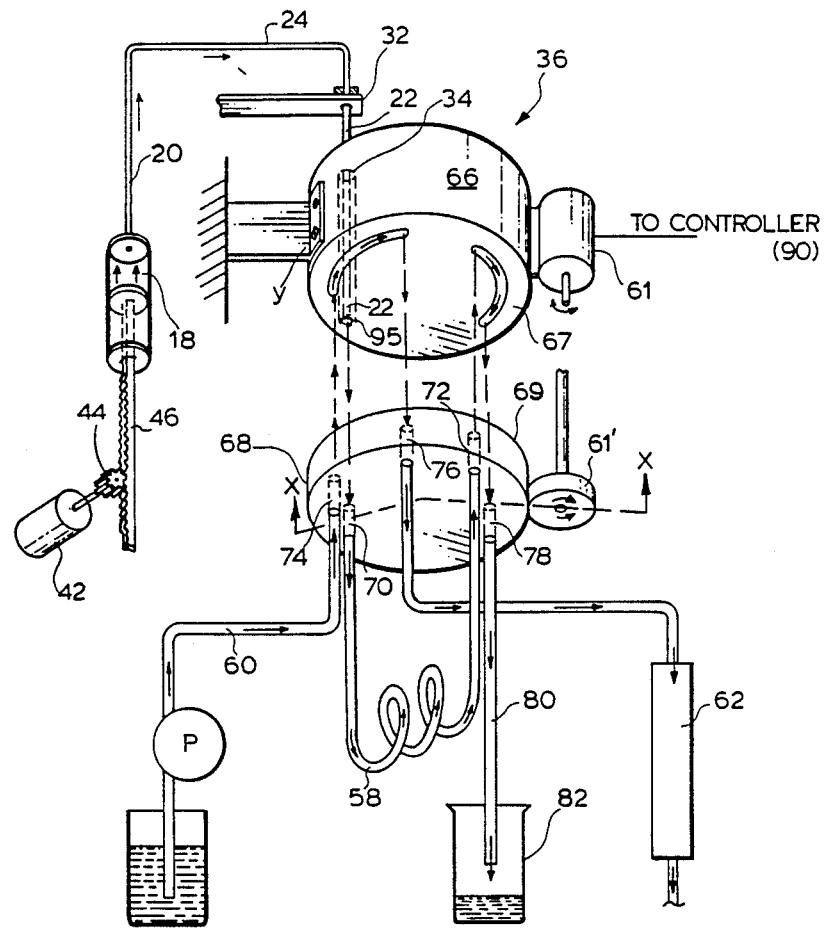
FIG. 4 is an exploded schematic view of the injector valve used with the present invention in the load position.

As can be seen from FIG. 4, the valve 36 is switched at this stage so that one end of a sample loop 58, connected to a first port 70 on the second element 68 of the valve 36, is aligned and in fluid communication with a tube-receiving passage 34 located in the first element 66 of the valve 36. A solvent pressure line 60 coupled to a third port 74 on the second element 68 of the valve is in fluid communication through the first element 66 of the valve with a liquid chromatograph column 62 coupled to a fourth port 76 on the second element 68 of the valve. The injector tube 22, once the valve is switched to such load position, is lowered by the raising and lowering means 32 into the tube-receiving passage 34, as shown in FIG. 2.

Accordingly, now that the valve 36 is in the load position (see FIG. 4), the syringe means may be operated by activating the motor 42 thereof to thereby force a portion of the quantity of sample 16 contained in the syringe-loop 24 through the injector tube 22 and into the tube-receiving passage 34 and sample loop 58. The sample loop 58 at its other end is connected to a second port 72 on the second element 68 of the valve, which is in fluid communication when the valve is in the load position through the first element 66 with a fifth discharge port 78, as shown in FIG. 4.

Figure 5:
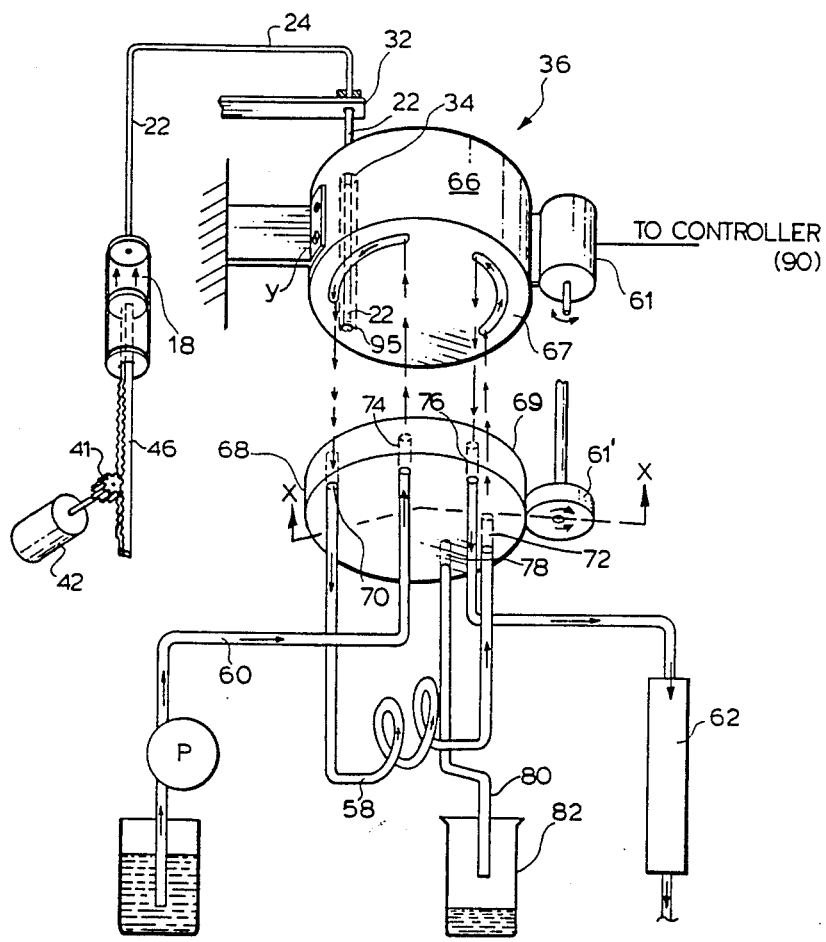
FIG. 5 is an exploded schematic view of the injector valve used with the present invention in the inject position.

The valve rotating means 61,61' are then activated, once the sample loop 58 has been filled, to rotate the second element 68 relative to the first element 66 so that the high pressure solvent line 60 comes into fluid communication through the first element 66 of the valve with one of ports 70,72 of the sample loop 58, and the liquid chromatograph column 62 connected to the fourth port 76 on the second element 68 comes into fluid communication with the other of said ports 70,72 of the sample loop 58, so that the valve 36 is now in an inject position (see FIG. 5). Accordingly, the high pressure solvent in line 60 is then allowed to flow to flush the portion of sample 16 in the supply loop 58 into the liquid chromatograph column for analysis.

The volume of the sample loop 58 can be less than the volume of the quantity of sample 16 drawn from the sample container or, it may be greater. However, pursuant to the invention it is necessary to at least once more operate the valve switching means to switch the valve back to the load position, operate the syringe means 18 to dispense the sample into the sample loop 58, and switch the valve-back to the inject position to again inject the new portion of sample into the liquid chromatograph column 62. This process may then be repeated until the quantity of sample in the syringe loop 24 is exhausted. The advantage of the above step is that an operator of the apparatus 10 is now able to sequentially analyze portions of the same quantity of sample. This increases the accuracy of the liquid chromatograph results because of the averaging effect from the number of runs.

After such steps, the injector tube 22 is raised by the raising means 32 to its original position, and the carousel means 12 is positioned so that a further selected one of the sample containers 14' is disposed vertically beneath the injector tube 22. The process is then ready to be repeated.

In order to properly sequence the raising and lowering motor 38, the syringe motor 42, the valve rotating means 61,61', and the carousel positioning means 26 to carry out the above method, a controller 90 may be used. Such controller may be a microprocessor chip, printed circuit, or other such means to allow the timely and proper sequencing of operator of each of the above components.

In order to eliminate the problem of contamination of the injected portion of sample due to remaining residual quantities of earlier samples remaining within the sample loop 58 and injector valve ports 70,72, a wash apparatus 100 may easily be incorporated into the sampler-injector apparatus 10 of the present invention. Accordingly, a wash reservoir 102 for containing a solvent may be provided, and a pump means 104 further provided to force the solvent through tubing means 106 into the syringe loop 24. Valve means 108, optionally controlled by the controller 90, may be placed at the junction of the tubing means 106 with the syringe loop, to allow flow of solvent through the syringe loop 24 when the injector tube 22 is in the tube-receiving passage 34, and the injector valve 36 is in the load position, as shown in FIG. 2. This configuration allows the solvent to purge the syringe loop 24, injector tube 22, valve ports 70,72, and the sample loop 58 connected thereto, of all previously remaining quantity of sample, prior to withdrawing the injector tube 22 from the valve 36 and subsequently positioning another sample container thereberneath. The flow of solvent through the above components may then easily exit from the injector valve through the fifth port 78 and into discharge tube 80 and thence into waste receptacle 82 (see FIG. 4) to ready the apparatus 10 for sampling of another sample quantity.

In the preferred embodiment, the wash reservoir 102 is a sealed container, and the pump means 104 is an air pump connected to the wash reservoir to pressurize the wash reservoir and thereby force solvent contained therein into tubing means 106.

In order to utilize as much as possible all sample quantity, in a preferred embodiment it is contemplated that the tube receiving passage 34 located within the first element 66 of the valve extend straight through the first element 66 to the face 67 thereof which is in bearing contact with the face 69 of the second element, as shown in FIG. 6. It is further contemplated that the injector tube have a substantially flat tip 95 lying in a plane perpendicular to the axis of the injector tube 22, so as to allow the injector tube 22 when inserted to the full depth of the tube-receiving passage 34 to lie flush against the face 69 of the second element 68, as shown in FIG. 6. In this embodiment, however, the first port 70 which in the load position is in communication with the tube-receiving passage 34 and first port 70 is contemplated as being narrower than the injector tube 22 to prevent passage of the tube 22 into the first port 70. Accordingly, then, all of the portion of sample forced into the injector valve 36 may be transferred directly to the sample loop 58 through the second element 68 of the valve 36, and may subsequently be transferred to the liquid chromatograph column 62 upon the valve being switched from the load position (FIG. 4) to the inject position (FIG. 5) by rotation of the second element 68 relative to the first element 66.

Although the disclosure describes and illustrates preferred embodiments of the invention, it is to be understood that the invention is not limited to these particular embodiments. Many variations and modifications will now occur to those skilled in the art. For definition of the invention, reference is to be made to the appended claims.

The embodiments of the invention in which an exclusive property or privilege is claimed are defined as follows:

1. An automated sample-injector apparatus for use with a liquid chromatograph column, comprising:
    (a) a carousel means which holds and retains therein a plurality of sample containers;
    (b) syringe means connected by tubing means to an injector tube to form a syringe-loop;
    (c) means for positioning a selected one of the sample containers immediately beneath the injector tube;
    (d) means for lowering the injector tube into the selected sample container and withdrawing a quantity of sample therefrom into said syringe-loop, and for raising the injector tube from with the sample container;
    (e) means for positioning the carousel means to allow direct insertion of the injector tube into a multi-port injector valve having a tube-receiving passage therein;
    (f) means for operating the syringe means to inject a portion of the sampled quantity from the syringe-loop into the injector valve when the injector tube is positioned in the tube-receiving passage, and further into a sample loop connected at both its ends to the injector valve; and
    (g) means for switching the valve by rotating one portion of the valve and keeping another portion of the valve containing the tube-receiving passage stationary to switch the sample loop from being in fluid communication with the tube-receiving passage to being connected at one end thereof to a supply of pressurized solvent, and at the other end thereof to a liquid chromatograph column;
    wherein the pressurized solvent flushes the portion of sample contained in the sample loop and injects it into the liquid chromatograph column for analysis.

2. The automated sample-injector apparatus as claimed in claim 1, further comprising means for supplying solvent to said tubing means and injector tube to purge said tubing means, injector tube, and sample loop of residual sample, comprising:
- a wash reservoir for containing a solvent;
- pump means to force said solvent into and through said tubing means; and
- valve means to allow addition of said solvent to said tubing means when said injector tube is in said tube-receiving passage and said sample loop is in fluid communication with said tube-receiving passage.

3. The automated sample-injector apparatus as claimed in claim 2 wherein said wash reservoir is a sealed container and said pump means is an air pump operatively connected to said wash reservoir to inject a quantity of air into said reservoir to pressurize the solvent located therein and to force said solvent into said tubing means.

4. The automated sampler-injector apparatus as claimed in claim 2 wherein said carousel is a substantially circular disc having an axis of rotation perpendicular to the plane of the disc and passing through its centre, said disc having a plurality of orifices parallel to said axis and located along a common radii about the periphery of said disc for holding and retaining said plurality of sample containers, and having at least one aperture passing in a straight line through the thickness of said disc.

5. An automated sample-injector apparatus for use with a liquid chromatograph column, comprising:
  I. carousel means adapted to hold a plurality of sample containers in a substantially horizontal plane, having at one location thereon an aperture;
  II. means for removing a quantity of sample from one of said sample containers, and injecting a portion of said quantity directly into a multi-port injection valve means, comprising:
    (a) an elongate, hollow injector tube having a substantially flat tip lying in a plane perpendicular to the axis of said tube;
    (b) means for rotating said carousel means to allow positioning of a selected one of said sample containers vertically beneath said injector tube and to allow positioning of said aperture vertically beneath said injector tube;
    (c) means for lowering said injector tube from an original position to a first position and for raising said injector tube back to said first position and for lowering to a second position within a tube-receiving passage in said injector valve means;
    (d) syringe means operable by an electric motor;
    (e) tubing means connecting said syringe means to said injector tube to allow said syringe means when activated by said electric motor to draw a quantity of sample from said sample container into said injector tube and tubing means; and
    (f) means to activate said electric motor to cause said syringe means to inject said portion of said quantity through said injector tube directly into said injector valve;
  III. said injector valve means adapted to receive said injector tube in said tube-receiving passage and further receive said injected portion of said quantity of sample and transfer said portion to said liquid chromatograph column to be analyzed, comprising:
    (a) a non-rotatable first element having said tube-receiving passage extending therethrough along a straight line to a face thereof;
    (b) a second element rotatably mounted on said first element and having a face axially adjacent to and in bearing contact with said face on said first element;
    (c) rotating means for rotating said face on said second element relative to said face on said first element to switch the injector valve means from a load position to an inject position;
    (d) a first port in said second element for connection at one end thereof to one end of a sample loop, said first port at its other end being narrower than the flat tip of the injector tube whereby the flat tip can lie flush against the face of the second element;
    (e) a second port in said second element for connection at one end thereof to said other end of said sample loop;
    (f) a third port in said second element for connection at one end thereof to a pressurized supply of liquid solvent;
    (g) a fourth port in said second element for connection at one end thereof to said liquid chromatograph column;
    (h) a fifth port in said second element for connection at one end thereof to a discharge tube;
    wherein said second element, when rotated relative to said first element to said load position by said rotating means has said first port aligned with said tube-receiving passage so as to be in fluid communication therewith, said second port in fluid communication through said first element with said fifth port, and said third port in fluid communication through said first element with said fourth port; and
    wherein said second element, when rotated relative to said first element to said inject position by said rotating means, has either of said first port or said second port in fluid communication through said first element with said third port, and said other of said first port or said second port in fluid communication through said first element with said fourth port.

6. A method for automatically sampling a quantity of sample and injecting in consecutive sequence portions of said quantity into a liquid chromatograph column for analysis, from each of a plurality of sample containers, comprising the steps of:
  (a) positioning a carousel member containing a plurality of sample containers so that a selected one of the sample containers is disposed vertically beneath an injector tube connected by tubing means to a syringe means;
  (b) lowering said injector tube from an original position into the selected sample container, and operating said syringe means to draw up a quantity of said sample through said injector tube into said tubing means;
  (c) raising said injector tube to its original position, and removing the selected sample container from beneath said injector tube so as to expose a multi-port injector valve vertically beneath said injector tube;
  (d) switching said multi-port injector valve so that one end of a sample loop, connected to a first port on a second element of said valve, is aligned and in communication with a tube-receiving passage located in a first element of said valve;
  (e) lowering said injector tube into said tube-receiving passage;

(f) operating the syringe means to force a portion of the quantity of sample contained in said tubing means through said injector tube and into said sample loop, said sample loop connected at its said other end to a second port on said second element of said valve;

(g) rotating said second element of said injector valve relative to said first element so that a means for flushing said portion of sample from the sample loop, connected to a third port on said valve, is in fluid communication with one of said ends of said sample loop, and a liquid chromatograph column connected to a fourth port on said second element is in fluid communication with said other of said ends of said sample loop, thereby flushing the sample from the sample loop and into said chromatograph column;

(h) repeating steps (d), (f) and (g) at least once;

(i) raising said injector tube to said original position; and (j) positioning said carousel member so that a further selected one of the sample containers is disposed vertically beneath said injector tube.

7. The method as claimed in claim 6, step (h) thereof further comprising the step of repeating steps (d), (f) and (g) until the quantity of sample contained in said tubing means is exhausted.

8. The method as claimed in claim 6, further introducing the steps after item thereof;

(h') switching said multi-port injector valve so that said one end of a sample loop connected to said first port on said second element of said valve, is aligned and in communication with said tube-receiving passage located in said first element of said valve;

(h") opening a valve to allow flow of a solvent into said tube means and through said injector tube, sample loop, and out a discharge tube connected to a fifth port on said injector valve, to thereby purge any residual sample; and (h''') closing the valve.

9. The method as claimed in claim 6, said second element of said injector valve having a flat surface axially adjacent and in bearing contact with a flat surface on said first element, said tube-receiving passage extending through said first element to said flat surface thereon, said injector tube having a flat tip lying in a plane perpendicular to the axis of the tube, step (e) of such method further comprising:

lowering said injector tube into said tube receiving passage wherein said flat tip abuts said flat surface on said second element.

10. The method as claimed in claim 6, said carousel member comprising a substantially circular disc having an axis of rotation perpendicular to the plane of the disc and passing through its center, said disc having a plurality of orifices parallel to said axis of rotation and located along a common radii about the periphery of the disc for holding and retaining said plurality of sample containers, and having at least one aperture passing in a straight line through the thickness of the disc, said step of positioning a carousel member comprising rotating said disc so that a selected orifice holding a selected sample container is disposed vertically beneath said injector tube, said step of removing the selected sample container from beneath the injector tube comprising rotating the disc so as to align said aperture vertically beneath said injector tube.

* * * * *